United States Patent [19]
Pfreundschuh

[11] Patent Number: 5,643,759
[45] Date of Patent: Jul. 1, 1997

[54] METHOD FOR PREPARING BISPECIFIC MONOCLONAL ANTIBODIES

[75] Inventor: Michael Pfreundschuh, Homburg/Saar, Germany

[73] Assignee: Biotest Pharma GmbH, Dreieich, Germany

[21] Appl. No.: 327,254

[22] Filed: Oct. 21, 1994

[30] Foreign Application Priority Data

Oct. 30, 1993 [DE] Germany .................. 43 37 197.3

[51] Int. Cl.$^6$ .................. C12P 21/08; C12N 5/12; C07K 16/00; C07K 16/18
[52] U.S. Cl. .................. 435/70.21; 435/172.2; 435/328; 435/335; 435/343.1; 530/387.3; 530/388.23; 530/388.73
[58] Field of Search .................. 435/70.21, 240.27, 435/172.2; 530/387.3, 388.23, 388.73, 388.75, 388.8, 388.85

[56] References Cited

FOREIGN PATENT DOCUMENTS

| 9105871 | 5/1991 | WIPO. |
| 9107437 | 5/1991 | WIPO. |
| 9208802 | 5/1992 | WIPO. |

OTHER PUBLICATIONS

Hombach, A et al., Int. J. Cancer, 55:830–836, Nov. 11, 1993.
Sahin, V.et al, Cancer Res., 50:6944–6948, Nov. 1, 1990.
Ferrini, S. et al., Int. J. Cancer, 48:227–233, 1991.
Renner, C., Ann. Hematol., 65(Suppl):A109, Abst #316, Oct. 4–7, 1992.
J. Titus, et al. The Journal of Immunology vol. 139, No. 9, pp. 3153–3158 (1987).
Proc. Natl. Acad. Sci. USA, vol. 83, pp. 1453–1457, Mar. 1986 "Hybrid Hybridoma Producing a Bispecific Monoclonal Antibody that . . . ".
Nature, vol. 316, Jul. 25, 1985, "Specific Targeting of Cytotoxic T Cells by Anti–T3 Linked to Anti–Target Cell Antibody".
Int. J. Cancer, vol. 42, pp. 455–459, 1988, "Activation of Mononuclear Cells to be Used Hybrid Monoclonal Antibody–Induced . . . ".
J. Immunol. vol. 144, pp. 2891–2898, 1990, "Targeted Cytotoxic Cells in Human Peripheral Blood Lymphocytes".
Nature, vol. 341, Sep. 1989, "CD3–Negative Killer Cells Express Zeta TCR as Part of a Novel Molecular Complex".
Science, vol. 214, pp. 24–30, 1981, "Natural Killer Cells": Their Role in Defenses Against Disease.
J. Immunol. vol. 136, No. 12, pp. 4480–4486, 1986, "The Relationship of CD16 (LEU–11) and LEU–19 (NKH–1) Antigen Expression . . . ".
J. Immunol, vol. 138, No. 4, pp. 1297–1302, 1987, "Phenotypic and Functional Characterization of Recombinant in . . . ".
J. Exp. Med. vol. 164, pp. 814–825, 1986, "Dissection of the Lymphokine–Activated Killer Phenomenon. Relative Contribution of . . . ".
J. Exp. Med. vol. 160, pp. 1686–701, 1984, "Production of Target–Specific Effector Cells Using Hetero–Cross–Linked Aggregates . . . ".
J. Immunol, vol. 139, No. 9, pp. 3153–3158, 1987, "Human K/Natural Killer Cells Targeted with Hetero–Cross–Linked . . . ".
Int. J. Cancer Supplement 7 pp. 15–18, 1992, "Targeting of T or NK Lymphocytes Against Tumor Cells by Bispecific . . . ".

*Primary Examiner*—Susan A. Loring
*Attorney, Agent, or Firm*—Sprung Horn Kramer & Woods

[57] ABSTRACT

The present invention relates to a method for the selective preparation of hybridoma cell lines which produce a murine monoclonal antibody (MAK) of the IgGl class with a high capacity for including NK cell-relate cytotoxicity against human CD16 antigen by co-culturing the hybridoma cells in the selection medium with unstimulated human NK (natural killer) cells. The invention furthermore relates to a cell line A9 of the DSM deposit number ACC 2148 obtainable in this manner, and a MAK obtainable therefrom, and a method for the preparation of bispecific MAK's by the fusion of an anti-CD30 cell line HRS-3 with hybridoma cell lines, which is obtained by the above-mentioned selection process, expecially with the A9 line of DSM deposit number ACC 2148 obtaining especially the bispecific MAK of the HRS-3/A9 cell line with the DSM deposit number ACC 2142. These bispecific MAK's are suitable for the treatment and for the shrinking of established human tumors, especially human Hodgkin's tumors.

4 Claims, 8 Drawing Sheets

-■-, C10-HYBRIDOMA CELLS;
-+-, A9-HYBRIDOMA CELLS; -*-, HRS3-HYBRIDOMA CELLS;

METHOD FOR PREPARING BISPECIFIC MONOCLONAL ANTIBODIES

The present invention relates to a method for the selective preparation of hybridoma cell lines which produce a murine monoclonal antibody (MAK) of the IgG1 class with a high capacity for inducing NK cell-related cytotoxicity against human CD16 antigen by co-culturing the hybridoma cells in the selection medium with unstimulated human NK (natural killer) cells.

The invention furthermore relates to a cell line A9 of the DSM deposit number ACC 2148 obtainable in this manner, and an MAK obtainable therefrom, and a method for the preparation of bispecific MAK's by the fusion of an anti-CD30 cell line HRS-3 with hybridoma cell lines, which is obtained by the abovementioned selection process, especially with the A9 line of DSM deposit number ACC 2148, obtaining especially the bispecific MAK of the HRS-3/A9 cell line with the DSM deposit number ACC 2142.

These bispecific MAK's are suitable for the treatment and for the shrinking of established human tumors, especially human Hodgkin's tumors.

The application of bifunctional monoclonal antibodies (Bi-MAK) for the treatment of tumors has been published by several groups of workers. The basis of all such works is the idea of breaking through the body's tolerance of the tumor by directly targeting the tumor cells with cytotoxic effector cells. The previous use of bispecific monoclonal antibodies as immunomodulators has consisted mainly of aiming the cytolytic activity of T cells against tumor cells through the CD3/T cell receptor complex (CD3/TCR complex) [Stearz US, Bevan, M. J.: Proc. Acad. Sci. USA 83: 1453–1457 (1986); Perez et al., Nature 316: 354 (1985)]. However, this had the disadvantage that a previous in vitro stimulation of the T-lymphocytes by an additional activation signal was necessary [Pupa S. M. et al: Int. J. Cancer 42: 455 (1988); Garrido M. A. et al: J Immunol 144: 2891 (1990)].

Another sub-population of human lymphocytes having the ability to lyse tumor cells is represented by natural killer cells (NK cells). As regards their cellular morphology these are large, granulated lymphocytes (LGL) and their immune phenotype is characterized by the absence of the CD3/TCR complex and by the expression of CD2, CD56 and CD16 antigens [Anderson P. et al: Nature 341: 159–162 (1989); Herberman R. B., Ortaldo, J. R.: Science 214: 24 (1981); Lanier L. L. et al: J Immunol 136: 4480 (1986)]. In contrast to T cells, NK cells show direct cytolytic activity against a series of "NK-cell-sensitive" tumor cells without prior activation. However, the majority of fresh and cultured tumor cells are relatively resistant to the anti-tumor action of dormant peripheral NK cells, which are not rendered capable of developing cytolytic activity against part of these NK-cell-resistant tumor cells until activated with interleukin-2 (IL-2) [Ferrini S. et al: J Immunol 138: 1297 (1987). Phillips J. H., Lanier L. L.: J Exp Med 164: 814 (1986)]. The CD16 antigen is a low-affinity receptor for the Fc part of complexed immunoglobulins (=Fc-gamma-III receptor) with a molecular weight of 50–70 kDa from which several cDNA clones have been isolated and sequenced cDNA clone. Numerous functional studies of the Fc-gamma-III-receptor have demonstrated its importance as the one effective activation antigen of NK cells. At the same time, biological functions of NK cells have been found which mediate biological functions of NK cells such as ADCC through the Fc-gamma-III receptor, the effectiveness of which in the use of monoclonal antibodies is subclass related. On the basis of the functional importance of the CD16 antigen for the activation of NK cells, a selective induction of tumor cell lysis via CD16 through bispecific antibodies therefore appeared to be especially promising. Actually it was possible with hetero conjugates of anti-CD16 antibodies and anti-DNP (dinitrophenyl phosphate) and tumor cell associated antibodies to induce selective lysis of DNP-coupled chicken erythrocytes [Karpovsky B. et al: J Exp Med 160: 1686 (1984)] and tumor cells of a human colonic carcinoma cell line established in vitro [Titus J. A. et al: J Immunol 139: 3153 (1987)] and murine T cell line [Garrido M. A. et al: J Immunol 144: 2891 (1990)] by unstimulated and IL-2-activated NK cells. Titus J. A. et al [J Immunol 139: 153] described a chemically crosslinked Bi-MAK against CD16 and a melanoma antigen which effectively inhibited tumor growth in vivo in the naked mouse. Bi-MAK's against CD16 and tumor antigens which were obtained by hybrid hybridoma technology (tetradoma technology) are described in works of Ferrini et al. [Int J Cancer Suppl 7: 15 (1992) and Ring, D. [Cetus, PCT/US91/16949]. These tetradomas produce Bi-MAK's, which link the CD16 antigen and epidermal growth factor receptor and multi-drug resistance antigen. Likewise Fanget et al. [Medarex, PCT/US90/05981] describe Bi-MAK against CD16 and tumor-associated antigens.

Impeding the growth of tumors with the bispecific MAK's is thus possible, but not a complete regression of established human tumors.

It is therefore the purpose of the present invention to develop CD16 MAK's which by themselves and in conjunction with known MAK's have the ability to induce a maximum NK cytotoxicity whereby the growth of human tumors will not be just impeded, but instead a complete remission of established human tumors will be achieved.

This purpose is achieved by the invention by preparing hybridoma cell lines which produce a murine MAK of the IgG1 class against human CD16 antigen and have a high activity as regards the induction of NK cell-related cytotoxicity, by co-culturing in the selection medium the hybridoma cell lines obtained by a method known in itself (Köhler/Milstein) with unstimulated human NK cells, especially granulocytes, and selecting the cells with the highest die-off rate.

Surprisingly it was found that the hybridoma cells, which form CD16 antibodies with an especially high cytotoxicity-inducing activity, have the highest die-off rate when they are co-cultured with dormant NK cells.

In accordance with the invention, the determination of the highest die-off rates is performed by comparison with a known anti-CD16 MAK, such as VEB 13, for example.

In this manner the cell line A9 of the DSM Deposit Number ACC 2148 is obtained, which has MAK's with the above-named properties.

This line or its MAK's selected specifically in the manner of the invention bind, as inhibition experiments show, to epitopes on the CD16 antigen which are remote from the binding epitope of known anti-CD16 MAK's, such as 3G8 (IgG1-Kappa, Dianova, Hamburg, Germany) or Leu 11b (commercially available), the MAK derived from line A9 attacking a binding point far away from the epitope of the known 3G8, and the MAK obtained from a line C10 attacking one somewhat nearer to it. Furthermore, the MAKA9 prepared according to the invention binds but very weakly to soluble recombinant human CD16, while the known antibodies referred to above bind more strongly. This shows that A9 recognizes epitopes other than the known anti-CK16 MAK's.

The MAK derived from A9 is a lambda subtype of mouse IgG1.

The MAK's derived from the A9 cell line prepared according to the invention are capable of inducing in lymphocytes a cytological activity against the corresponding antibody-producing hybridoma cells, while an approximately 60% specific lysis occurs, which has not been achieved with the MAK's heretofore known.

Thus these hybridoma cells, especially the cells derived from the A9 line, fuse in a manner known in itself with HRS-3-hybridoma cells to form tetradomas (hybrid hybridomas), from which bispecific MAK's are obtained, especially from the line HRS-3/A9 with the DSM Deutsche Sammlung Von Mikroorganismen Und Zell Kulturen GmbH, Mascheroder Weg 1 B, D-38124 Braunscgweig Deposit Number ACC 2142, which are effective in the suppression of human tumors, especially in the suppression of established Hodgkin's tumors, the Bi-MAK on the one hand being more effective than the individual components A9 and HRS-3, and on the other hand more effective than the previously known BiMAK's named above with which only a restraint of tumor growths can be achieved, but not a complete regression.

The hybridoma cells and the MAK's and Bi-MAK's derived from them can be prepared in the following manner:

Immunized BALB/C mouse spleen cells are fused with mouse myeloma cells in a known manner. The cell suspension obtained is then co-cultured in the selection medium in the presence of unstimulated human NK cells, especially granulocytes and, if desired, peripheral blood lymphocytes (PBL). By comparing the anti-CD16 activity with known CD16 antibodies, such as VEP 13, for example, the hybridoma cells are selected which have the highest die-off rates. By this principle of reverse cytotoxicity the line A9, especially, with the DSM Deposit Number ACC 2148 is obtained.

This line is propagated in a known manner by injection into BALB/c mice and obtained from the ascites by chromatographic purification.

To prepare the Bi-MAK's, especially Bi-MAK's HRS-3/A9 with two light chains of different classes (lambda and kappa), HGPRT-negative HRS-3 hybridoma cells (IgG1, kappa, subtype, active against Hodgkin's and Reed-Sternberg cell-associated CD30 antigen, described by Engert et al, 1990), are fused with A9 hybridoma cells treated, for example, with iodoacetamide. After testing for bispecific reactivity, for example by the detection of antibodies with different light-chain content by indirect immunofluorescence, the mixed tetradoma cell clone is obtained which has the strongest possible simultaneous expression of the two light chains, and then purified by chromatography.

Experiments in vivo with the Bi-MAK HRS-3/A9 in the treatment of human Hodgkin's tumors in SCID mice show that, in a majority of the animals tested, a complete remission of the tumors occurs.

The Bi-MAK HRS-3/A9 can be formulated by known methods, e.g., as a solution of lyophilizate, and serves for parenteral application in humans, while adjuvants and additives known to the expert can be present.

The invention will be further described by the following examples:

More specifically, "the cell line produces the described bispecific monoclonal antibody and secretes it into the culture medium. The antibody will be purified and reconstituted, for example, in PBS. This antibody preparation will be given to patients with tumors the neoplastic cells of which express the CD30 antigen and are refractory to standard chemo- and radiotherapy treatment. Such tumors are Hodgkin's disease (HD), anaplastic large cell lymphoma (ALCL) and HTLV-1-positive adult T-cell leukemia (ATL). Patients eligible for this treatment would have a life expectancy of a few months without this treatment and account for about 30% with ALCL and the majority of patients with ATL.

It is expected that the antibody will bind the patients' own natural killer cells onto the tumor cells and mediate a specific activation signal so that the patient's own killer cells will kill his tumor cells. The preclinical data show that the antibody in conjunction with the patient's killer cells is able to cure SCID mice from the patients' tumors.

In clinical practice the treatment of the respective patients consists of 10 mg/m$^2$ of the antibody which will be given intravenously by a 1-hour infusion to each patient. The treatment will be repeated weekly until either the patient is cured from his tumor or the tumor shows progressive growth despite the antibody treatment.

In addition to its therapeutic usefulness, the described bispecific monoclonal antibody can also be used to assay a person's Bi MAB-mediated natural killer cell capacity. This is accomplished by an in vitro cyctotoxicity assay (as described above) using defined concentrations of Bi MAB, the lymphocytes of the patient to be tested on the L640 Hodgkin's cell line.

The invention will be further described in the examples hereinbelow taken in conjunction with the accompanying drawings, wherein.

Figure 6:
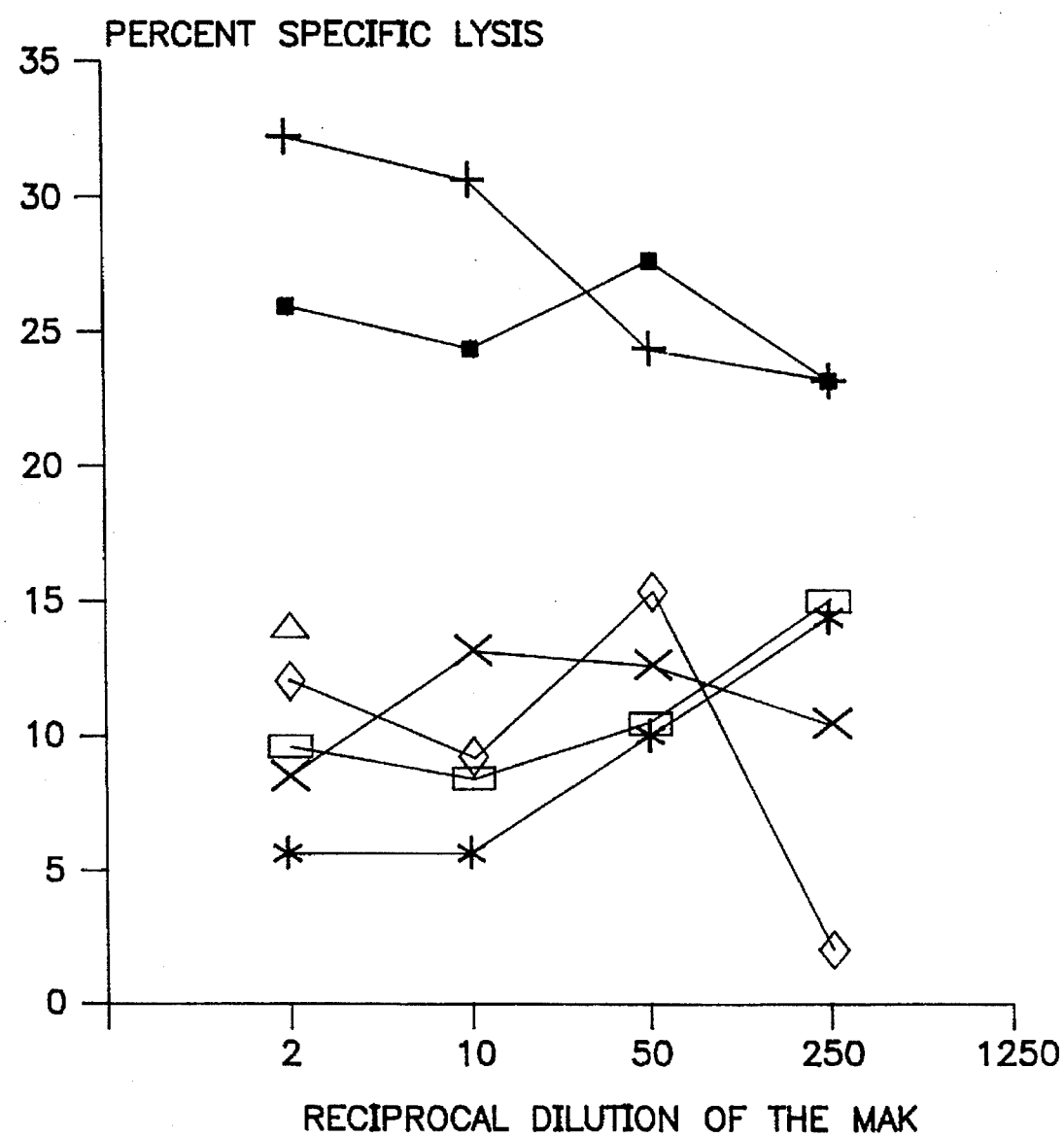
Figure 7A:
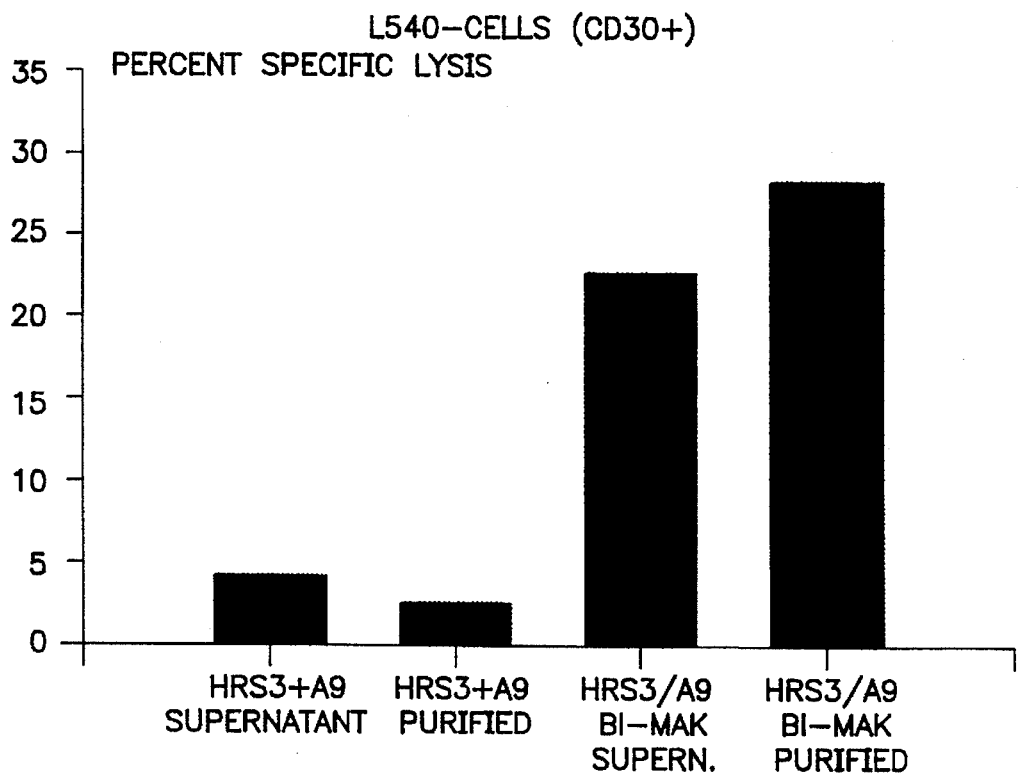
Figure 7B:
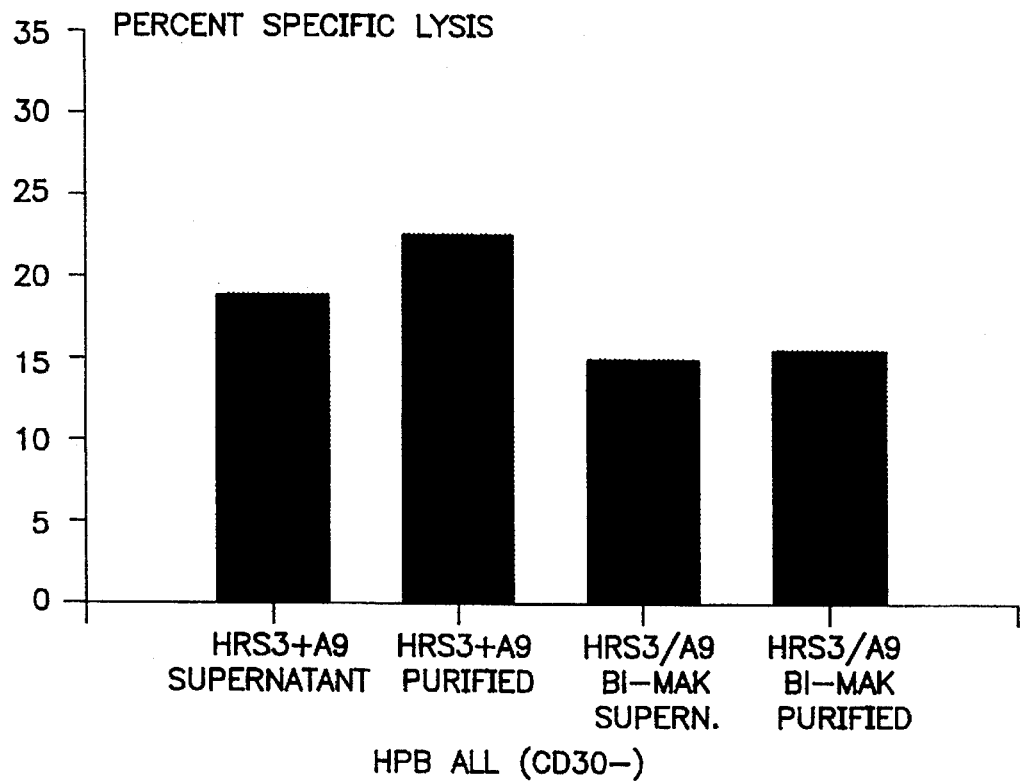
Figure 8:
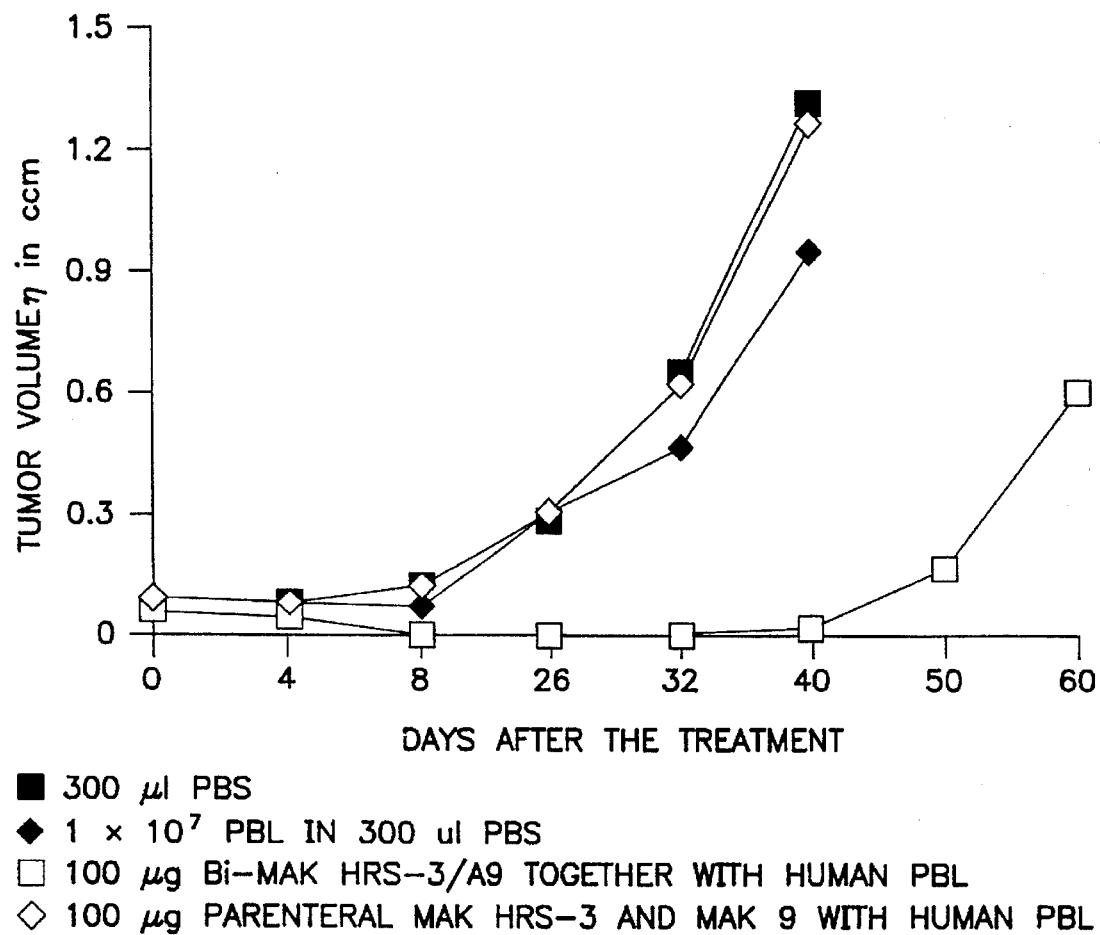

FIGS. 6 and 7 show the induction of a cytotoxicity (specific lysis) mediated by NK-cells against human tumor cells in vitro (CD30-antigen positive Hodgkin's lymphona cell line L540) of the claimed Bi-MAK HRS-3/A9 as well as of original antibodies HRS-3, A9 in accordance with procedure in Example 7; and FIG. 8 shows the regression of tumor growth of human Hodgkin's tumor in mice treated with the claimed Bi-MAK PIRS 3/A9 in comparison with non-treated animals in accordance with Example 8.

I. Preparation of A9 and C10 CD16-MAK

EXAMPLE 1

Immunization, Fusion and Cloning of Monoclonal Antibodies A9 and C10

For the immunization, female BALB/c mice 3 to 4 months old were used. 3–5×107 freshly isolated granulocytes in 0.5 ml PBS were injected peritoneally into the animals at two-week intervals. The first injection was performed in the form of a 1:1 emulsion in complete Freund's adjuvant, the second and third injection as 1:1 emulsions in incomplete Freund's adjuvant. The rest of the immunization steps were performed without adjuvant. Ten weeks later, on each of the four days preceding the planned fusion, the animals were given a booster injection of 5×107 granulocytes each.

The immunized spleen cells were fused with AG8-653 mouse myeloma cells in a ratio of 2:1 in the presence of polyethylene glycol. The fused cell suspension was washed once and cultured in the selection medium (RPMI 1640, 10% fetal calf serum), 4 mM glutamine, HAT: hypoxanthine 13.6 mg/l; aminopterin 0.17 mg/l and 10 μg/ml insulin. Fourteen days after the fusion, supernatants of cultures which showed hybridoma growth were tested for production of anti-CD16. For that purpose peripheral blood lymphocytes (PBL) and granulocytes were incubated with 10 μl of test supernatant fluid or control antibody. The commercially obtainable CD16 antibody VEP13 was used as the control MAK. The bound MAK was detected by means of an FITC-tagged mouse antibody in the cytofluorometer. Of 1021 supernatants tested, 4 showed a CD16-specific binding pattern.

After 4 cloning steps using the limiting dilution method (seeding density 0.3 cells per culture) these 4 clones were isolated. A9 is a murine IgG1-MAK with a lambda light chain, and C10 is a murine IgG1-MAK with a kappa light chain. Both show a significant binding to NK cells.

EXAMPLE 2

In vivo production and purification of MAK A9 and C10

The anti-CD16 MAK's A9 and C10 were produced in large quantities in vivo by intraperitoneal injection of A9/C10 hybridoma cells into BABL/c mice. One week before the hybridoma cell injection the mice were primed intraperitoneally with 1.0 ml of Pristan. 8 to 14 days after the hybridoma cell injection ascites fluid could be taken.

The MAK's A9 and C10 were then precipitated from the ascites fluid by ammonium sulfate precipitation (4% saturation). Then followed additional purification of the antibodies by anion exchange chromatography. This was performed with a Mono-Q® column (Pharmacia, Freiburg).
II. Comparison of MAK A9 and C10 with other anti-CD16 MAK's

EXAMPLE 3

Figure 1A:
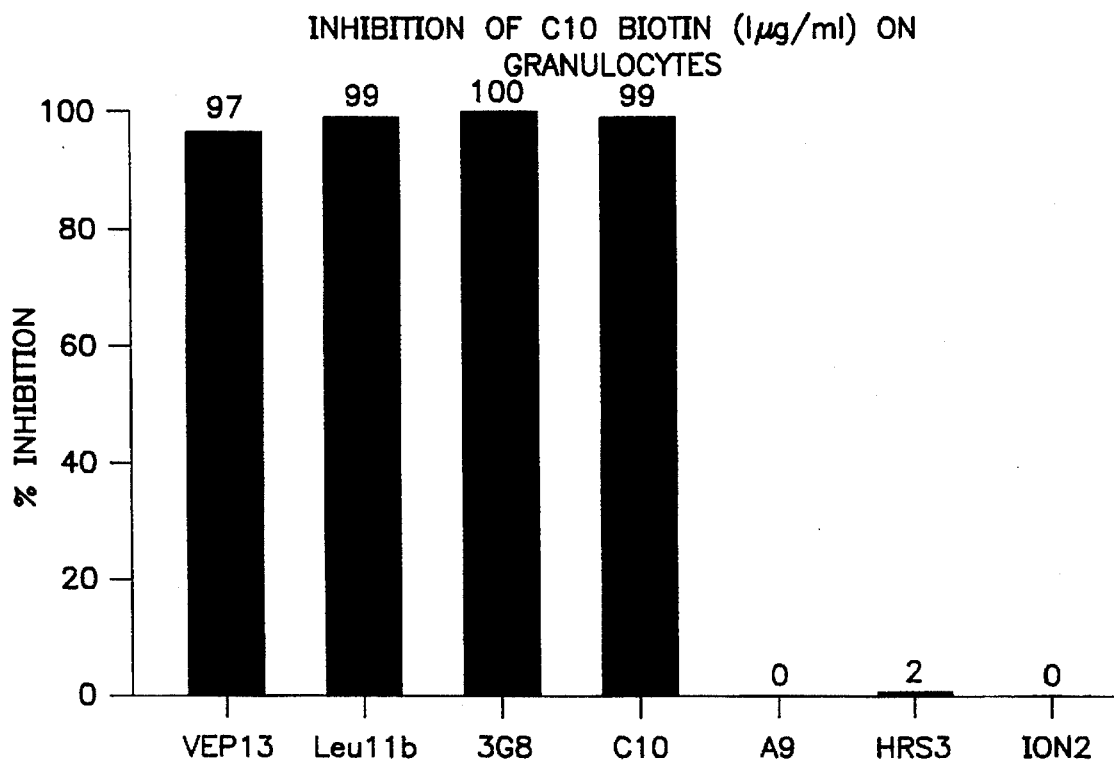
FIG. 1 shows the results of inhibition tests of C10 and A9 Biotin.
Figure 1B:
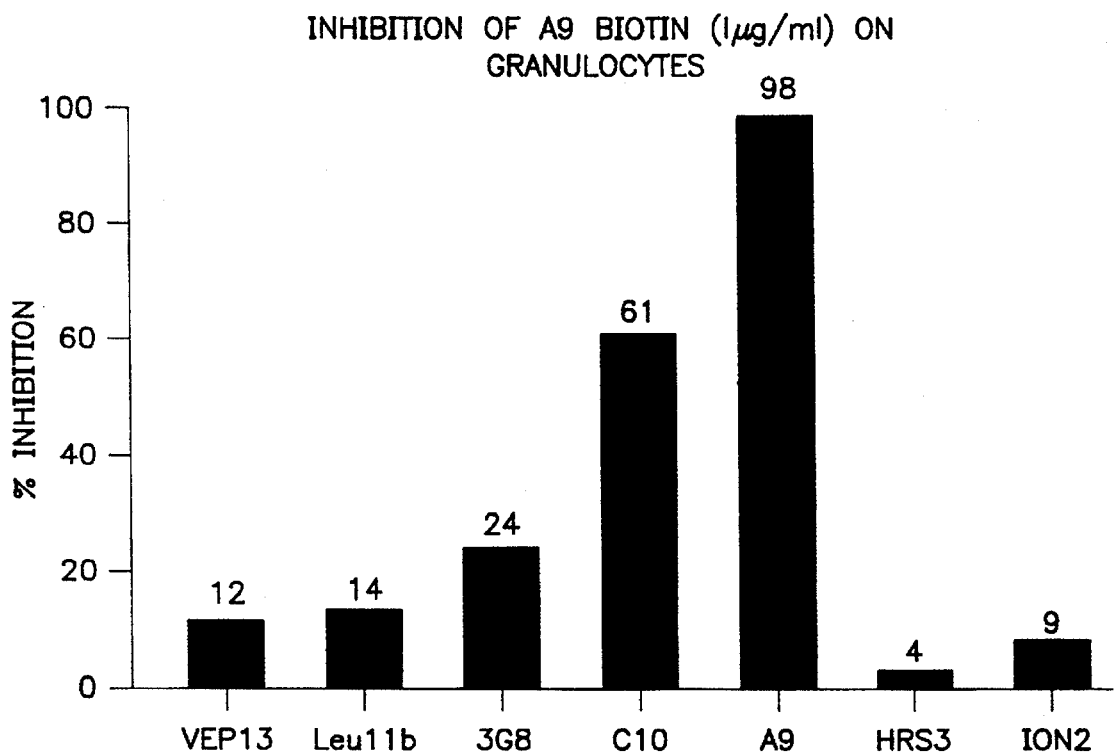
Figure 2A:
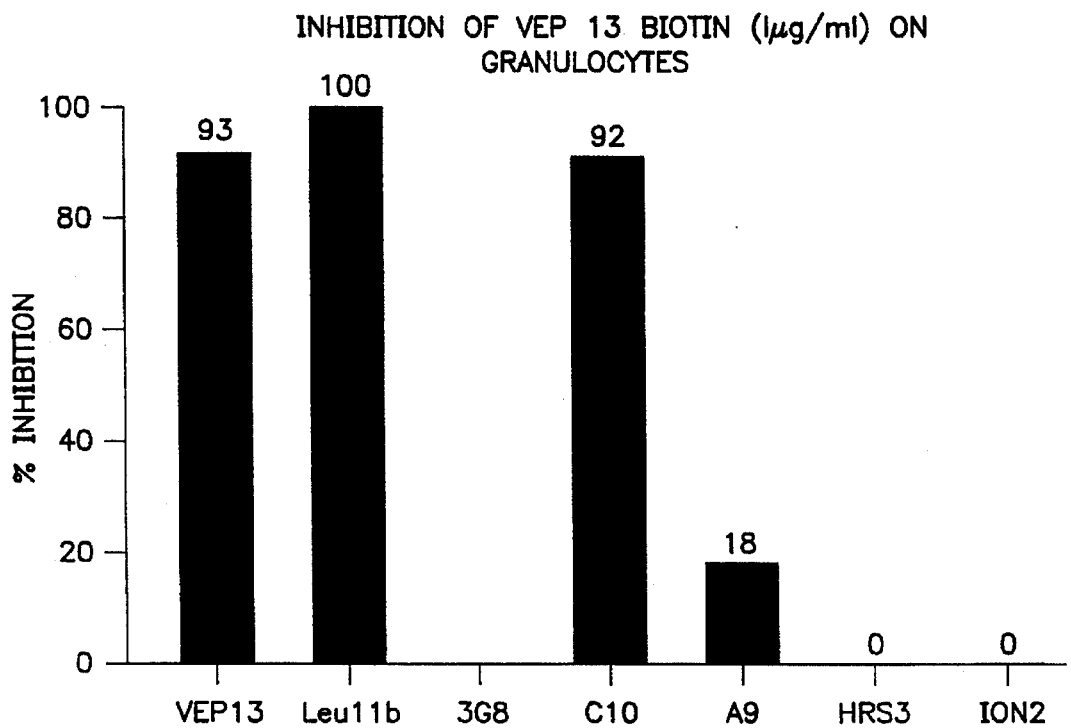
FIG. 2 shows the results of inhibition tests of VEP 13 Biotin and 3G8 FITC.
Figure 2B:
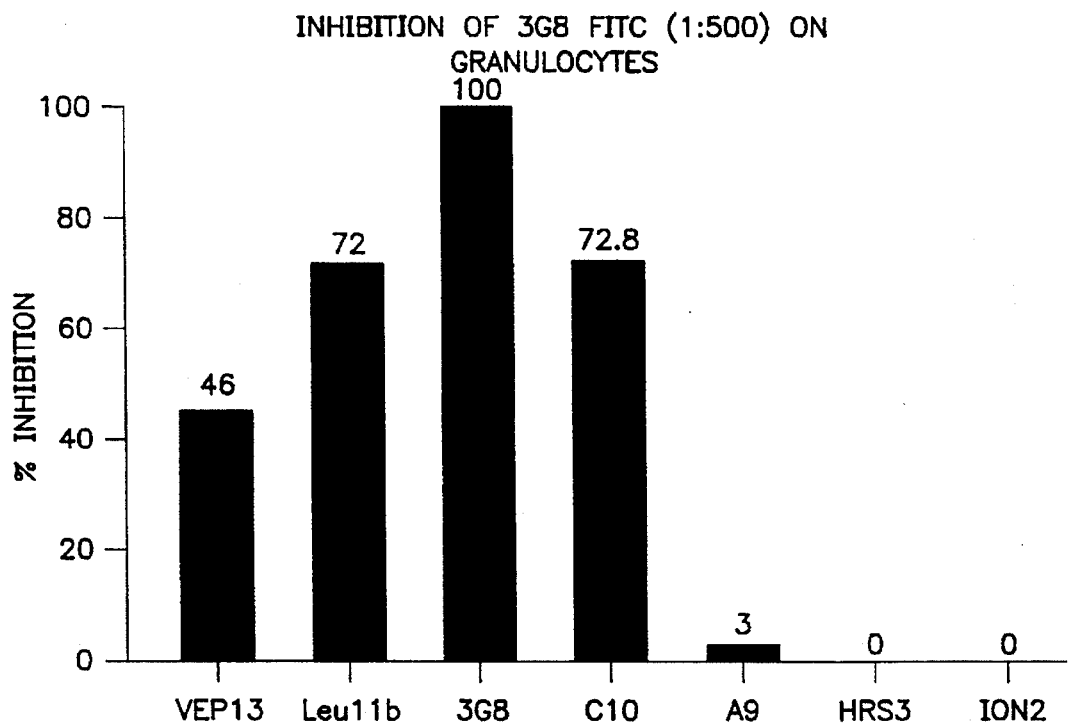

Inhibition Experiments in the Determination of Epitopes (FIGS. 1 and 2)

According to Perussia et al. (J Immunol 133: 180 (1984)) there exist at least three different, nonoverlapping epitopes on the CD16 antigen. In order more precisely to define the epitopes of the CD16 antigen of the CD16 MAK's A9 and C10 developed in the invention, inhibition assays were performed with biotinylated A9 and C10 MAK's and the commercially available CD16 MAK's 3G8, VEP13 and Leu11b by means of direct and indirect immunofluorescence tests with peripheral lymphocytes, followed by permeation cytometric evaluation. In these assays the antibodies 3G8, VEP13 and Leu11b recognize the same epitopes on the CD16 antigen or else epitopes situated very close to one another [Perussia et al. (1984)]. FIGS. 1 and 2 present representative results of the inhibition tests. The tagged antibodies in each case were the biotin-conjugated antibodies A9, C10, VEP13 and the FITC-conjugated antibody 3G8. Accordingly, C10 biotin was completely inhibited by 3G8, VEP13 and Leu11b, and conversely C10 completely inhibited the anti-CD16 antibody VEP13 biotin completely and it partially inhibited 3G8-FITC. The inhibition of VEP13 biotin by C10 was dose-related, both by the complete antibody and by C10-F(ab')2 fragments. A9 biotin, however, was inhibited only partially by 3G8 and C10 and not inhibited at all by Leu11b and VEP13. At the same time C10 inhibited the binding of A9 biotin to a far greater degree than 3G8. A9 itself inhibited none of the rest of the tagged antibodies. Otherwise, the tested anti-CD16 antibodies showed a mutual inhibition similar to that described by Perussia et al. (1984). These results indicate that A9 and C10 bind other epitopes on the CD16 antigen, A9 an epitope farther removed from the epitopes recognized by the other MAK's, while the epitope recognized by C10 is closer to the epitope recognized by 3G8.

EXAMPLE 4

Figure 4:
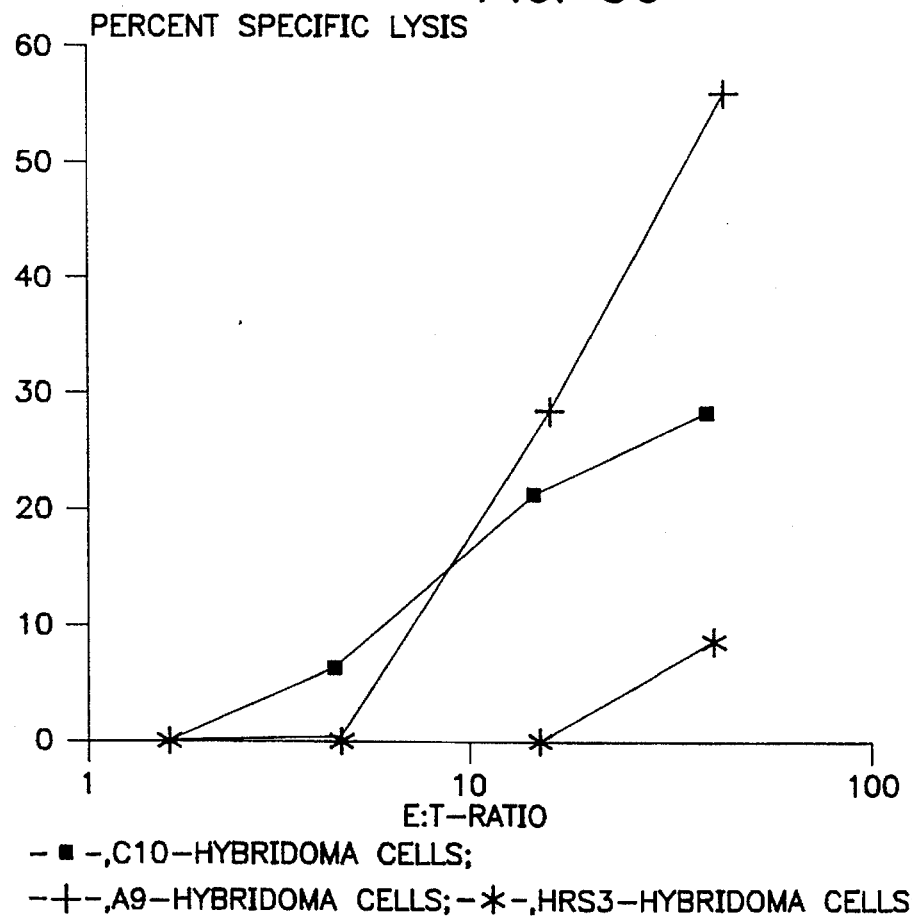
FIG. 4 shows the induction of NK-cell-related cytotoxicity (specific lysis) of the antibodies A9, C10 and HRS-3 against hybridoma cells producing CD16 MAK, in accordance with Example 5.

Binding of MAK A9 and C10 to Soluble Recombinant Human CD16 Antigen (FIG. 4)

Figure 3A:
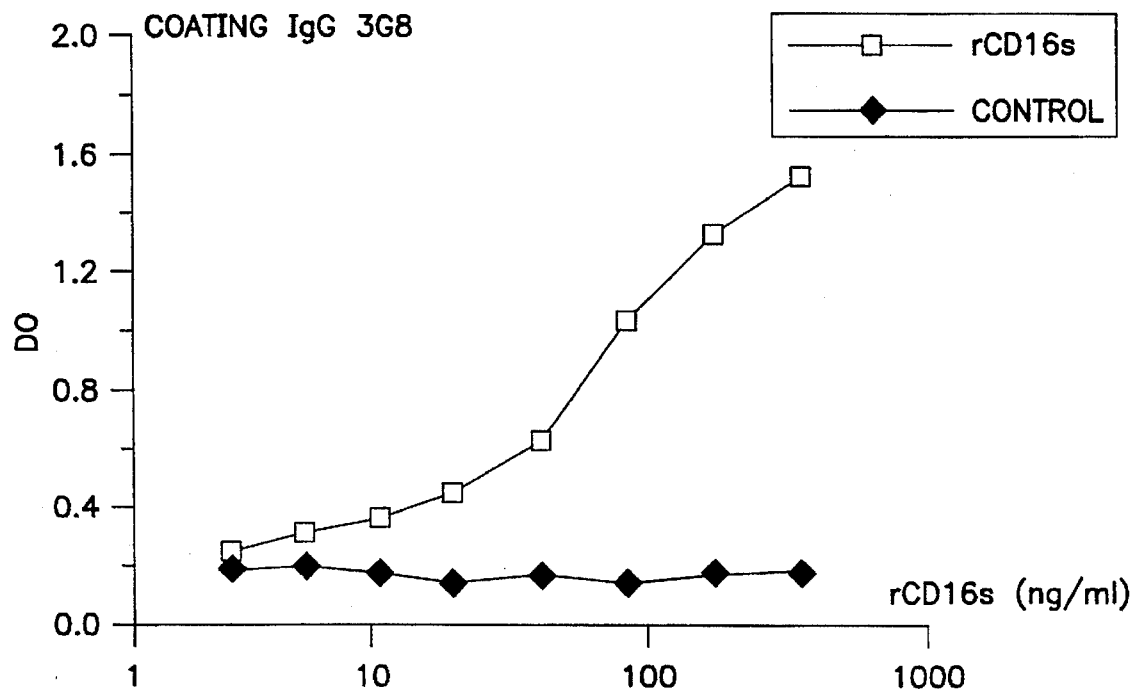
FIGS. 3A–3C shows the results of sandwich—ELISA tests with soluable recombinant human C D16.
Figure 3B:
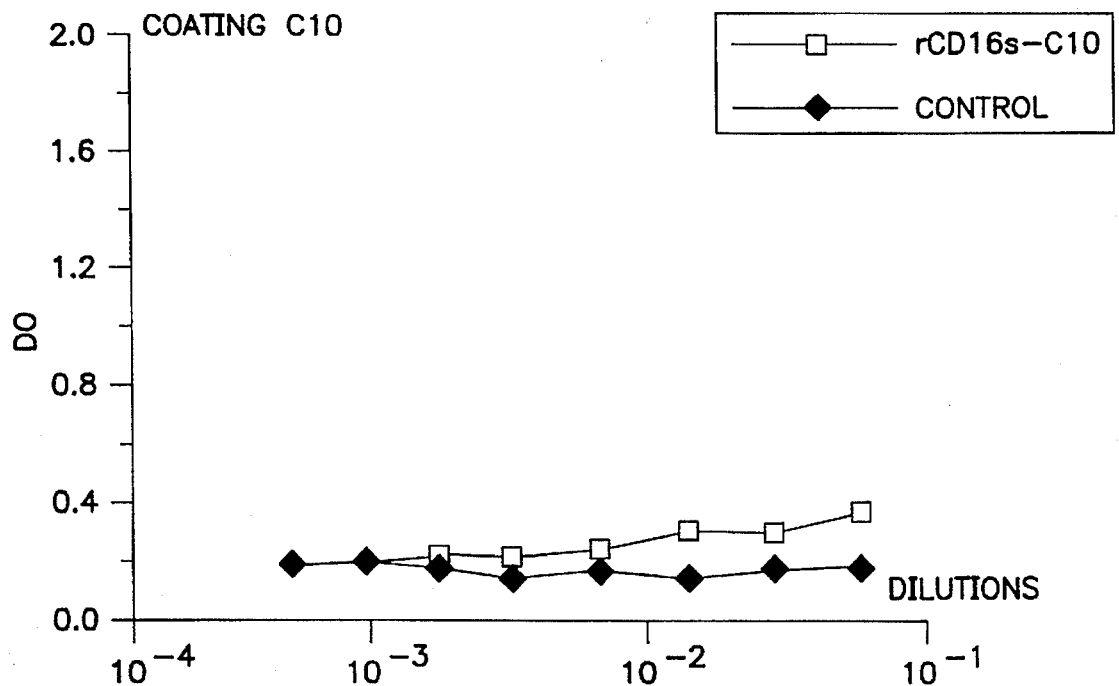
Figure 3C:
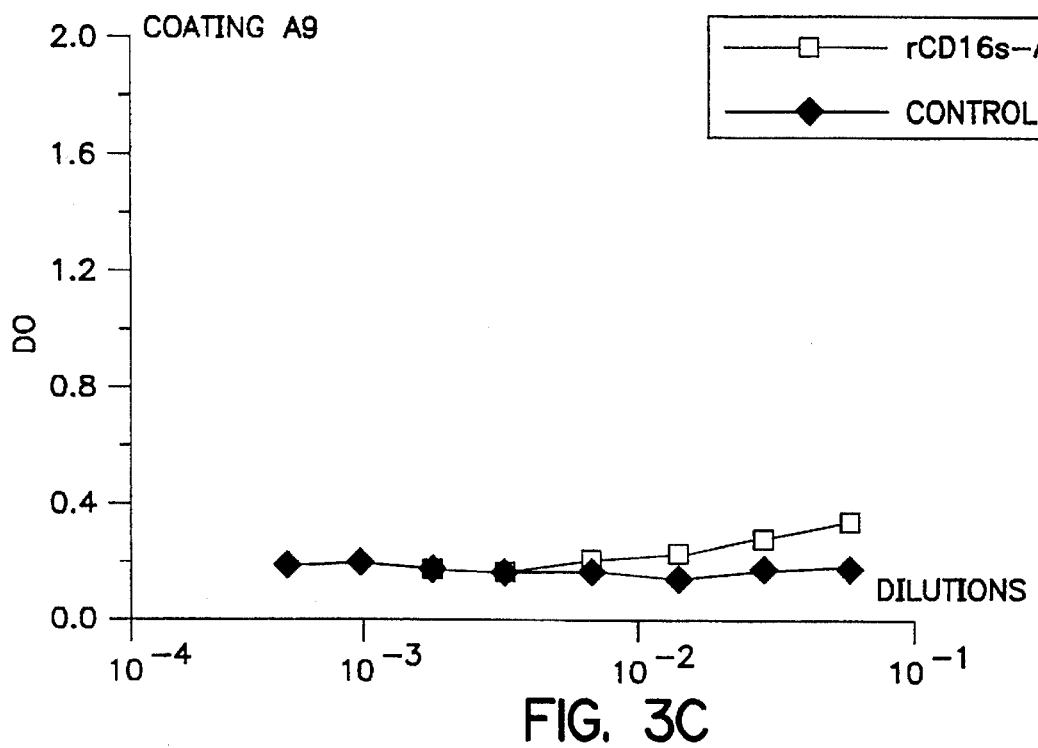

In a Sandwich-ELISA, the results of which are represented in FIG. 3A–3C, with soluble recombinant human CD16, it appeared that both A9 (3C) and C10 (3B) bind but very weakly to soluble recombinant human CD16 antigen, in contrast to the other CD16 MAK's (3A) referred to above. This signifies that both A9 and C10 behave differently in binding to soluble CD16 antigen than the rest of the antibodies. Since both antibodies, however, show a great affinity for cell-bound CD16, this cannot be explained by differences in affinity; instead, the ELISA results indicate that the epitopes on the CD16 antigen that are recognized by A9 and C10 are different from the epitopes that are recognized by other CD16 MAK's.

III. Biological activity of the A9 and C10 monoclonal antibodies

EXAMPLE 5

Induction of NK-cell-related Cytotoxicity Against Hybridoma Cells Producing CD16 MAK (FIG. 4)

For this purpose $5 \times 10^3$ hybridoma cells tagged with $^{51}Cr$ and mononuclear cells in 100 μl of medium in the ratios 45:1, 15:1, 5:1, and 1.5:1 were co-cultured for 12 hours and the specific lysis was determined from the release of the $^{51}Cr$. The results of this cytotoxicity test are represented in FIG. 4. It appeared that the newly developed antibodies A9 and C10, in contrast to the antibody HRS-3 used as control, were both capable of inducing cytolytic activity in lymphocytes against the hybridoma cells producing the corresponding antibody. The maximum hybridoma cell lysis induced by A9 was approximately 60% specific lysis, but the lysis that was induced by C10 amounted to only about 30% specific lysis.

IV. Bispecific monoclonal antibodies

EXAMPLE 6

Preparation of a Bi-MAK from MAK A9 and a Second MAK, HRS-3, Directed Against an Antigen Associated with Human Tumor To prepare bi-MAK's for the induction of cytotoxicity against human tumor cells, mediated by NK cells, HGPRT-negative HRS3 hybridoma cells IgG1-kappa were fused with A9 hybridoma cells treated with iodoacetamide. A total of 113 cell clones grew in the selection medium (HAT medium), of which 17 clones (=15%) showed bispecific reactivity. The test for bispecificity was performed by the demonstration of antibodies of different light-chain content by the indirect immunofluorescence test. The tetradoma cell clone that showed the strongest simultaneous expression of both light chains was repeatedly sub-cloned, established as a cell line, and the bispecific antibody separated therefrom was named HRS-3/A9. The separation of the bispecific antibody from the monospecific original antibodies HRS3 and A9 also produced by the tetradoma cells was performed out of murine ascites containing HRS-3/A9 by an FPLC-mono-Q® anion exchange chromatography. The total immune globulin fraction containing antibody variants produced by the tetradoma cells was then further fractionated by an FPLC-Mono-S® cation exchange chromatography. Comparison of the isoelectric points of the antibodies HRS3 and A9 by isoelectric focusing showed that the isoelectric point of A9 was situated further within the basic range than that of HRS3. For this reason, a pH (=5.9) was selected that was just below the isoelectric point of HRS3, so that the positive charge density in this antibody was the lowest and accordingly had to be eluted before HRS3/A9 and A9. The elution was performed with a discontinuous salt gradient with 50 mmol/l of MES, from 0 to 250 mmol/l NaCl.

Figure 5:
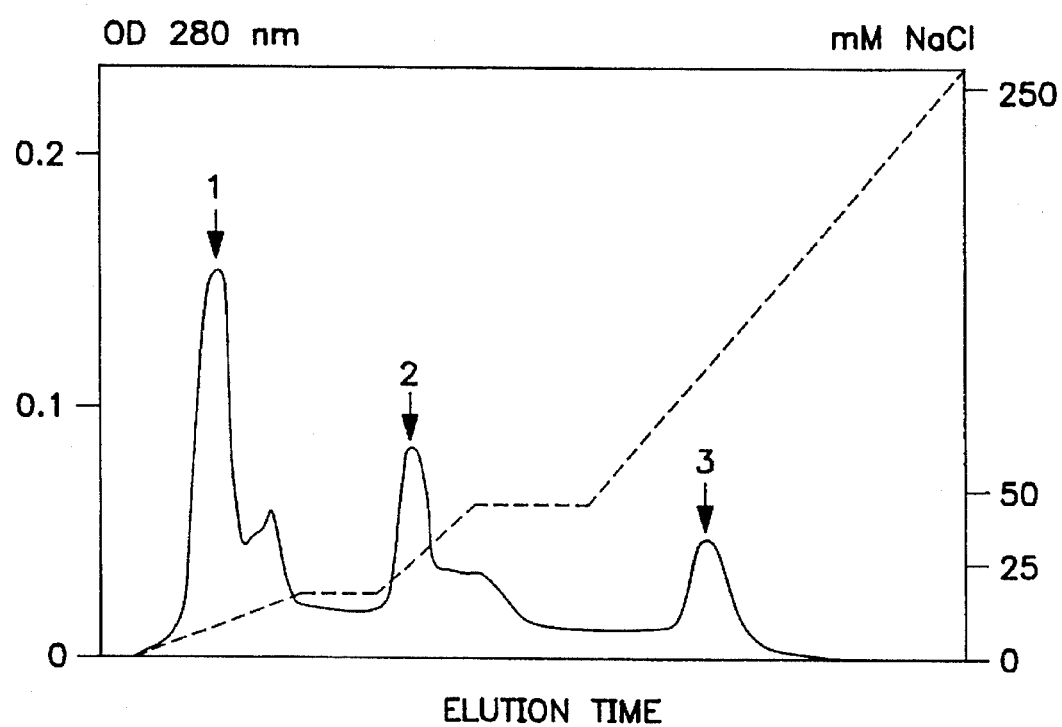
FIG. 5 shows a chromatogram concerning ion exchange chromatographic purification of the Bi-MAK from MAKA9 and MAK HRS-3 in accordance with the method described in Example 6. Thereby peak 2 shows the fraction containing the Bi-MAK for exhibiting bispecific activity.

FIG. 5 shows the resulting chromatogram. The immunoglobulins were divided into 3 fractions (=3 peaks), which then were tested for their content of bispecific antibodies. The immunological testing of the 3 fractions by indirect immunofluorescence showed that 2 fractions (peak 2) contained the bispecific activity.

EXAMPLE 7

Induction of a Cytotoxicity Mediated by NK Cells Against Human Tumor Cells In Vitro (FIGS. 6 and 7)

Lymphocytes enriched with NK cells by a Percoll density gradient centrifugation showed but little cytolytic activity against the CD30-antigen-positive Hodgkin's lymphoma cell line L540 (14% specific lysis). However, when the bispecific antibody HRS-3/A9 was used a definite increase in the cytolytic activity against L540 cells was observed, both in cell culture supernatant fluid containing bispecific antibodies (up to 27% specific lysis), and in purified bispecific antibody (up to 32% specific lysis). The cytolytic activity of the original antibodies HRS-3 and A9 with effector cells and of the bispecific antibody without effector cells, used as controls, was only between 5 and 15%. The results of this testing are represented in FIG. 6. The supernatant fluid was diluted 1:1, and the maximum concentration of the purified antibodies in the test batch was 5 µg/ml. Both were diluted reciprocally as stated. The E:T ratio was 20:1.

At the same time, this elevation of the lytic activity was specific for the CD30 cell line L 540. The bispecific antibody HRS3/A9 was able only in the case of L 540 cells to intensify the cytolytic activity of NK cells, while no increase was observed in the cytolytic activity against the CD30 cell line HPB-ALL, which showed a certain amount of spontaneous "NK-cell sensitivity". The results of this testing are represented in FIG. 7. The supernatant fluid was diluted 1:20, and the concentrations of the purified Bi-MAK amounted to 1 µg/ml. The E:T ratio was 20:1.

The results obtained with unstimulated peripheral blood lymphocytes (PBL) were equal to those obtained with concentrated NK cells. The induction of cytotoxicity by Bi-MAKHRS-3/A9 mediated by NK cells thus required no concentration of the NK cells. This is especially important in regard to any therapeutic use of this antibody in patients.

V. preclinical experiments with the Bi-MAK HRS-3/A9

EXAMPLE 8

Treatment of Human Hodgkin's Tumors in SCID Mice with Bi-MAK HRS-3/A9 and human PBL (FIG. 8)

Hodgkin's tumors were established by subcutaneous injection of a suspension of $1.5 \times 10^7$ cells of the human Hodgkin's cell line L540CY into the thoracic wall of 4 to 6-weeks-old female SCID mice. After the tumors had reached a diameter of at least 5 mm, groups of 10 tumor-bearing mice received intravenously 100 µg of Bi-MAK HRS-3/A9 or an equal amount of control antibody and $1 \times 10^7$ human PBL. In 10 out of 10 SCID mice with established human Hodgkin's tumors, a complete regression of the tumors was achieved by day 40, while all the other untreated mice showed advancing tumor growth, and when a tumor size of 10 mm diameter was reached they were killed. In 4 of the specifically treated mice a resumption of tumor growth occurred (recidivism) after 60 days (FIG. 8). In another series a complete remission was achieved by the use of HRS-3/A9 and human PBL's. The animals in that case were given, on day 0, an injection of 1) 300 µl PBS 2) $1 \times 10^7$ human peripheral blood lymphocytes PBL in 300 µl of PBS 3) 100 µg Bi-MAKHRS-3/A9 with human PBL 4) a mixture of 100 µg of parenteral MAKHRS-3 and MAKA9 together with human PBL.

The growth of the tumor is represented as the average tumor volume (ccm) of all tumor-bearing animals of a treatment group.

It will be appreciated that the instant specification and the claims are set forth by way of illustration and not limitation, and that various modifications and changes may be made without departing from the spirit and scope of the present invention.

I claim:

1. A method for preparing bispecific MAB's, which comprises fusing a hybridoma cell, A9, which produces a murine MAB of class IgG1 with a high capacity for inducing NK cell-related cytotoxicity, whereas said MAB is specific for human CD16 antigen, with hybridoma cells HRS-3 which binds human CD30 antigen to form a tetradoma HRS-3/A9 of deposit account number ACC 2142 thereby to obtain a bispecific MAB and isolating bispecific MAB, the hybridoma cell line A9 having been produced by a. co-culturing hybridoma cell line A9 of deposit number ACC 2148 which produces CD 16 MAB with unstimulated human NK cells, b. determining the die-off rate of the hybridoma cells and then c. selecting the hybridoma cells with the highest die-off rate.

2. A method according to claim 1, wherein the co-culturing according to step a is performed in the presence of granulocytes and the determination of the die-off rates according to step b is performed by comparison with a control CD16 antibody.

3. The bispecific MAB which is produced or producible by the process of claim 1.

4. The tetradoma HRS-3/A9 which is produced on producible by the process of claim 1.

* * * * *

UNITED STATES PATENT AND TRADEMARK OFFICE
CERTIFICATE OF CORRECTION

PATENT NO. : 5,643,759
DATED : July 1, 1997
INVENTOR(S) : Pfreundschuh, Michael

It is certified that error appears in the above-indentified patent and that said Letters Patent is hereby corrected as shown below:

Col. 8, line 60   Delete " on " and substitute -- or --

Signed and Sealed this

Ninth Day of June, 1998

Attest:

BRUCE LEHMAN

Attesting Officer          Commissioner of Patents and Trademarks